United States Patent [19]

Joseph

[11] Patent Number: 5,161,532
[45] Date of Patent: Nov. 10, 1992

[54] INTEGRAL INTERSTITIAL FLUID SENSOR

[75] Inventor: Jose P. Joseph, Menlo Park, Calif.

[73] Assignee: Teknekron Sensor Development Corporation, Menlo Park, Calif.

[21] Appl. No.: 511,329

[22] Filed: Apr. 19, 1990

[51] Int. Cl.$^5$ ............................................. A61B 5/00
[52] U.S. Cl. .................................... 128/635; 204/403
[58] Field of Search ................. 128/635, 760; 204/403

[56] References Cited

U.S. PATENT DOCUMENTS

| | | | |
|---|---|---|---|
| 4,240,438 | 12/1980 | Updike et al. | 128/635 |
| 4,294,258 | 10/1981 | Bernard | 128/635 |
| 4,432,366 | 2/1984 | Margules | 128/635 |
| 4,450,842 | 5/1984 | Zick et al. | 128/635 |
| 4,534,356 | 8/1985 | Papadakis | 128/635 |
| 4,655,880 | 4/1987 | Liu . | |
| 4,750,496 | 6/1988 | Reinhart et al. . | |
| 4,781,798 | 11/1988 | Gough | 128/635 |
| 4,832,034 | 5/1989 | Pizziconi et al. | 128/632 |
| 4,919,141 | 4/1990 | Zier et al. | 128/635 |
| 4,953,552 | 9/1990 | DeMarzo | 128/635 |
| 4,975,175 | 12/1990 | Karube et al. | 128/635 |

FOREIGN PATENT DOCUMENTS

| | | | |
|---|---|---|---|
| 3713060 | 11/1987 | Fed. Rep. of Germany | 128/635 |
| 2426904 | 1/1980 | France | 128/635 |
| 1394171 | 5/1975 | United Kingdom . | |
| 2204408 | 11/1988 | United Kingdom . | |

OTHER PUBLICATIONS

"A Novel Blood Glucose Monitoring Method An Isfet Biosensor Applied to Transcutaneous Effusion Fluid", J. Kimura, N. Ito, T. Kuriyama, J. Electrochem. Soc., vol. 136, No. 6, Jun. 1989.
K. Commann, "Working with Ion-Slective Electrodes" 6 *Application of Ion-Selective Electrodes,* 1979, pp. 188–189, FIG. 62.

*Primary Examiner*—Lee S. Cohen
*Assistant Examiner*—Krista M. Pfaffie
*Attorney, Agent, or Firm*—Limbach & Limbach

[57] ABSTRACT

An integral interstitial fluid sensor for application to the skin of a person or an animal for the detection of chemical components of tissue fluid is disclosed. The fluid sensor comprises a substrate of a porous material for the passage of the interstitial fluid therethrough. At least two electrodes are provided. One of the electrodes has two sides, with one side mounted on the substrate. The electrode is also of a porous material and permits the passage of the interstitial fluid from one side through to the second side which is generally opposite the one side. A layer of chemical is on the second side. The layer of chemical comprises a chemical for reaction with one component of the fluid, mixed in a mediating agent. The electrodes generate an electrical signal upon the detection of the reaction of the one component of the fluid with the chemical. The electrical signal is received by a detector and a display is generated, indicating the amount of the one component detected. Finally, a pump for sucking the fluid from the skin into the sensor is disclosed.

7 Claims, 1 Drawing Sheet

INTEGRAL INTERSTITIAL FLUID SENSOR

TECHNICAL FIELD

The present invention relates to a fluid sensor which can be applied to the skin of a patient or an animal for the detection of chemical components of interstitial fluid, and more particularly, wherein the interstitial fluid sensor is an integral sensor.

BACKGROUND OF THE INVENTION

Apparatuses for measuring blood glucose concentration are well known. See, for example, U.S. Pat. No. 4,750,496. In an article entitled "Novel Blood Glucose Monitoring Method and ISFET Biosensor Applied to Transcutaneous Effusion Fluid" by J. Kimura, N. Ito, T. Kuriyama, published in J. Electrochem. Soc., Vol 136, No. 6, Jun. 1989, pp. 1744–1747, interstitial fluid was withdrawn via a pump and applied to an ISFET biosensor. The sensor was able to detect chemical components of the interstitial fluid.

The drawback of such an apparatus appears to be the cumbersome requirement of the pump, separate and apart from the sensor, and the requirement of drawing out a large amount of interstitial fluid in order to sense the chemical components therein. This prohibits the use of an interstitial fluid which can be "permanently" attached to a person or an animal for the detection of chemical components of the fluid on an "as needed" basis.

SUMMARY OF THE INVENTION

In the present invention, an integral interstitial fluid sensor is disclosed. The sensor is applied to the skin of a patient or animal, to detect the chemical components of the interstitial fluid. The sensor comprises a substrate of porous material which permits the passage of the interstitial fluid therethrough. At least two electrodes are provided. One of the electrodes has two sides, with one side mounted on the substrate. The one electrode is also of a porous material for the passage of the interstitial fluid from the one side in contact with the substrate through to the second side which is generally opposite the one side. A layer of chemical is on the second side. The layer comprises a chemical for reaction with one component of the interstitial fluid. The chemical is mixed in a mediating agent. The electrodes produce an electrical signal in response to the reaction of one component of the interstitial fluid with the chemical. Means for sucking the interstitial fluid from the skin into the sensor is provided. Finally a detector means receives the electrical signal generated by the electrodes and generates a display indicative of the amount of the one component in the interstitial fluid detected.

DETAILED DESCRIPTION OF THE DRAWINGS

Figure 1:
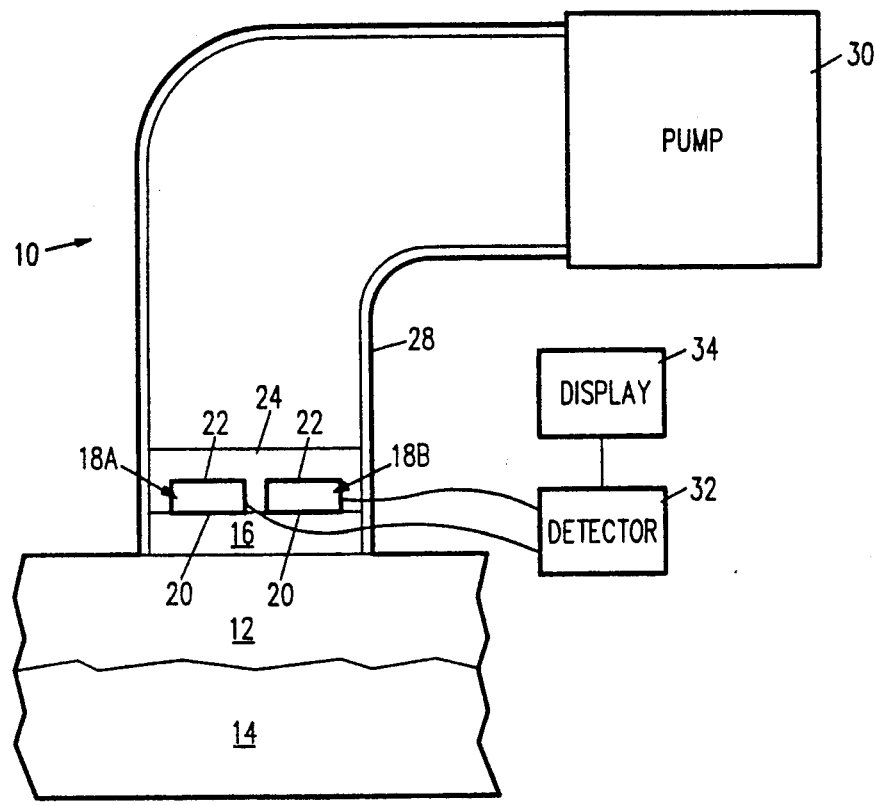
FIG. 1 is a cross-sectional side view, greatly exaggerated and enlarged, of one embodiment of an integral interstitial fluid sensor of the present invention.

Referring to FIG. 1, there is shown an enlarged, greatly exaggerated, cross-sectional side view of one embodiment of the integral interstitial fluid sensor 10 of the present invention. The sensor 10 can be applied to the skin 12 of a person or an animal. Interstitial fluid residing in the derms or the subcutis layer 14 beneath the epiderm skin layer 12 can be detected by the sensor 10.

The sensor 10 comprises a substrate 16 of a porous material. The substrate 16 is applied to the epiderm layer 12 or the outermost skin layer 12. The substrate 16 is of a porous material. In one embodiment, the substrate 16 is made of ceramic. In one embodiment shown in FIG. 1, two electrodes 18A and 18B are placed on the substrate 16. Each of the electrodes 18A and 18B has two sides, one side 20 is mounted on the substrate 16. Each of the electrodes 18A and 18B is also of a porous material and permits the passage of interstitial fluid therethrough from one side 20 through to the second side 22 which is generally opposite the one side 20.

A layer of chemical 24 is on the second side 22 of the electrodes 18A and 18B. The chemical 24 comprises a chemical for reacting with one component of the interstitial fluid, with the chemical mixed in a mediating agent.

The substrate 16, the electrodes 18A and 18B, and the chemical 24 are all contained in a vessel 28 with one end of the vessel 28 placed upon the skin or the epiderm layer 12. The other side of the vessel 28 is attached to a pump 30. The pump 30 sucks the interstitial fluid from the derm layer 14, through the epiderm layer 12, through the porous substrate 16 and through the electrodes 18A and 18B into the chemical layer 24, where it reacts with the chemicals. The reaction of the chemical 24 with the interstitial fluid produces an electrical signal which is picked up by the electrodes 18A and 18B. The electrical signal can be measured by a detector 32. The detector 32 is an amperometric detector and operates to detect the current generated by the electrodes 18A and 18B. The display of the amount of current in the electrical signal detected by the detector 32 indicates the amount of the one chemical component of the interstitial fluid.

In one embodiment, the sensor 10 is adapted to measure the glucose content of the interstitial fluid. The substrate 16 has the dimensions of approximately 2–4 $Cm^2$. The pump 30 applies a suction at a rate of approximately 200–400 torr. Each of the electrodes 18A or 18B can be 1 mm. Thus, a total volume of approximately 0.01 microliter of the sensor 10 needs to be wetted. At a sampling rate of approximately 0.4 microliter/min/$cm^2$, the entire electrodes 18A and 18B can be wetted in less than 2 seconds. The chemical 24 is an enzyme glucose oxidase and the mediator is immobilized on the electrodes 18A and 18B. The thickness of the enzyme chemical layer 24 can be approximately 10 micrometer.

Using an amperometric detector 32, having a display 34, with a mediator, the sensor 10 of the present invention avoids buffer and oxygen dependency. As previously stated, the substrate 16 can be made of a porous material such as ceramic. Each of the electrodes can be made by sputtering metal upon a porous substrate, again, such as ceramic. One of the electrodes 18A can be Pt sputtered upon a porous substrate, such as ceramic. The other electrode 18B can be Ag sputtered on ceramic and converted to AgCl electrochemically or by chemical treatment, e.g. by bringing Ag in contact with 1% FeCl$_3$ in 0.1 m HCl. One of the electrodes 18B operates as the reference electrode with the other operating as the working electrode 18A in an amperometric sensing measurement, which is well known in the art.

Figure 2:
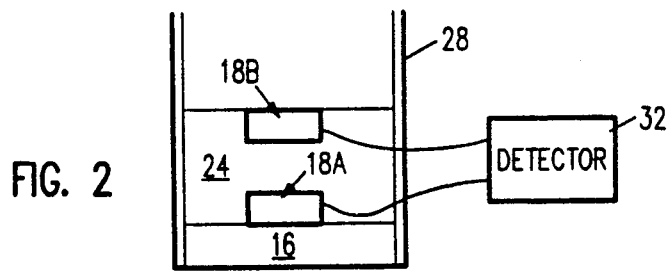
FIG. 2 is an enlarged, greatly exaggerated, cross-sectional view of a component of another embodiment of the integral interstitial fluid sensor of the present invention.

Referring to FIG. 2, there is shown another embodiment of the sensor 10 of the present invention. The difference between the embodiment shown in FIG. 2 and the embodiment shown in FIG. 1 is that in FIG. 2, only one of the electrodes 18A is mounted on the substrate 16. The second electrode 18B is mounted directly opposite the first electrode 18A with the layer of chemical 24 therebetween. Thus, in FIG. 2, the interstitial fluid passes substantially through the substrate 16 and through the first electrode 18A into the chemical layer 24. The second electrode 18B has one surface in contact with the layer of chemical 24 and a second surface generally opposite thereto. The second electrode 18B is also generally on a porous material. With the first electrode 18A also being of a porous material, the pump 30 can suck the interstitial fluid through the substrate 16 and into the chemical layer at 24.

Figure 3:
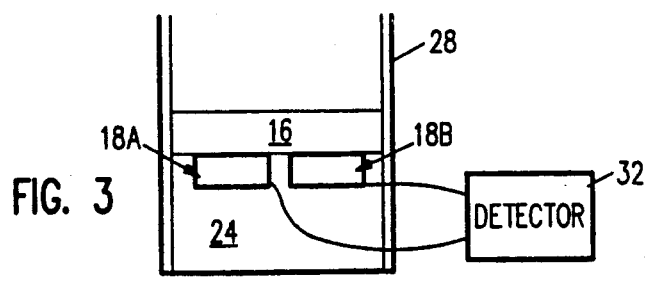
FIG. 3 is an enlarged, greatly exaggerated, cross-sectional view of a component of yet another embodiment of the integral interstitial fluid sensor of the present invention.

Referring to FIG. 3, there is shown yet another embodiment of the sensor 10 of the present invention. In FIG. 3, the two electrodes 18A and 18B have one side thereof mounted on the porous substrate 16. Each of the second side of the electrodes 18A and 18B faces and is in contact with the layer of chemical 24. Thus, in FIG. 3, the interstitial fluid passes substantially through the chemical layer 24 (possibly after passing through a layer of second porous material), and contacts the layer of chemicals 24 and the first and second electrodes 18A and 18B. The fluid then passes through the substrate 16. The pump 30 can suck the interstitial fluid through the layer 24 of chemical into the electrodes 18A and 18B and through the substrate 16.

There are many advantages to the integral interstitial fluid of the present invention. The particular advantage is that the volume of fluid sucked from the person or animal can be extremely small. Thus, the entire assembly can be made small, e.g. the size of a wrist watch. For measurement of certain chemical components in the interstitial fluid, such as glucose, the sensor 10 can be worn by a diabetic patient so the glucose measurement can be done "on demand." This will result in a convenient device for the continuous monitoring of glucose in tissue fluid which as known in the prior art, with the glucose in the interstitial fluid correlating to the glucose in blood.

What is claimed is:

1. An integral interstitial fluid sensor for application to the skin of a person or an animal for detection of chemical components of an interstitial fluid, said sensor, comprising:

a substrate of a porous material for passage of the interstitial fluid therethrough;

at least two electrodes: a first electrode and a second electrode;

said first electrode has two sides: a first side and a second side, said first side is mounted on said substrate with said second side generally opposite said first side, said first electrode is of a porous material for passage of the interstitial fluid through the two sides;

a layer of chemical in contact with said second side of said first electrode for reaction with one component of said interstitial fluid, mixed in a mediating agent;

said second electrode in contact with said layer of chemical;

said two electrodes for generating an electrical signal in response to the reaction of the one component of said interstitial fluid with said layer of chemical;

detecting means for receiving said electrical signal;

means for generating a display in response to said detecting means; and means for sucking said fluid from the skin through said substrate into said layer of chemical.

2. The sensor of claim 1 wherein said second electrode is mounted on said substrate, said second electrode has two sides with one side on said substrate and the other side generally opposite thereto, for the passage of the interstitial fluid through said two sides, and with said layer of chemical in contact with said other side of said second electrode.

3. The sensor of claim 1 wherein said second electrode has two sides with one side in contact with said layer of chemical, and the other side, generally opposite said one side, said second electrode for the passage of the interstitial fluid through the two sides.

4. The sensor of claim 1 wherein said substrate is ceramic.

5. The sensor of claim 1 wherein said first electrode comprises Pt mounted on said porous substrate.

6. The sensor of claim 5 wherein said second electrode is AgCl mounted on said porous substrate.

7. The sensor of claim 1 wherein said layer of chemical is glucose oxidase and said one component is glucose.

* * * * *